(12) United States Patent
Candau

(10) Patent No.: US 7,172,753 B2
(45) Date of Patent: Feb. 6, 2007

(54) PHOTOPROTECTIVE UV-SCREENING COMPOSITIONS COMPRISING TRIAZINE/DIBENZOYLMETHANE/ DIARYLBUTADIENE COMPOUNDS

(75) Inventor: Didier Candau, Bièvres (FR)

(73) Assignee: L'Oreal, Paris (FR)

( * ) Notice: Subject to any disclaimer, the term of this patent is extended or adjusted under 35 U.S.C. 154(b) by 764 days.

(21) Appl. No.: 10/463,432

(22) Filed: Jun. 18, 2003

(65) Prior Publication Data

US 2004/0028626 A1    Feb. 12, 2004

Related U.S. Application Data

(63) Continuation of application No. PCT/FR01/03639, filed on Nov. 20, 2001.

(30) Foreign Application Priority Data

Dec. 18, 2000 (FR) ................... 00 16517

(51) Int. Cl.
*A61Q 19/04* (2006.01)
*A61Q 19/00* (2006.01)
*A61O 8/02* (2006.01)
*A61K 8/00* (2006.01)

(52) U.S. Cl. .................. 424/59; 424/60; 424/400; 424/401

(58) Field of Classification Search ............... 424/59, 424/60, 400, 401
See application file for complete search history.

(56) References Cited

U.S. PATENT DOCUMENTS

| 6,093,385 | A  | 7/2000 | Habeck et al. |
| 6,238,649 | B1 | 5/2001 | Habeck et al. |
| 6,387,355 | B2 | 5/2002 | Heidenfelder et al. |
| 6,391,289 | B2 | 5/2002 | Heidenfelder et al. |
| 6,436,373 | B1 | 8/2002 | Habeck et al. |

FOREIGN PATENT DOCUMENTS

| EP | 1 051 963 A1   | 11/2000 |
| FR | 2 757 055 A1   | 6/1998  |
| FR | 2 757 057 A1   | 6/1998  |
| WO | WO 98/00099 A1 | 1/1998  |

*Primary Examiner*—Shelley A. Dodson
(74) *Attorney, Agent, or Firm*—Buchanan Ingersoll & Rooney PC

(57) ABSTRACT

Topically applicable, photostable cosmetic/dermatological UV-screening compositions suited for photoprotecting the skin and the hair, comprise (a) at least one UV-screening dibenzoylmethane compound, (b) at least one UV-screening 1,3,5-triazine compound that is photosensitive in the presence of a dibenzoylmethane compound, and (c) a 1,3,5-triazine photostabilizing amount of at least one 4,4-diarylbutadiene compound, formulated into a topically applicable, cosmetically/dermatologically acceptable support therefor; the weight ratio of the 4,4-diarylbutadiene compound(s) to the dibenzoylmethane compound(s) is characteristically greater than 2.5 and the subject compositions are advantageously devoid of any cinnamate sunscreen.

34 Claims, No Drawings

PHOTOPROTECTIVE UV-SCREENING COMPOSITIONS COMPRISING TRIAZINE/DIBENZOYLMETHANE/DIARYLBUTADIENE COMPOUNDS

CROSS-REFERENCE TO PRIORITY/PCT APPLICATIONS

This application claims priority under 35 U.S.C. § 119 of FR-00/16517, filed Dec. 18, 2000, and is a continuation of PCT/FR01/03639, filed Nov. 20, 2001 and designating the United States (published in the French language on Jun. 27, 2002 as WO 02/49599 A2; the title and abstract were also published in English), both hereby expressly incorporated by reference.

BACKGROUND OF THE INVENTION

1. Technical Field of the Invention

The present invention relates to a cosmetic or dermatological composition for topical application, in particular for photoprotecting the skin and the hair, comprising, in a cosmetically acceptable support:
(a) at least one dibenzoylmethane derivative,
(b) at least one 1,3,5-triazine derivative that is photosensitive in the presence of a dibenzoylmethane derivative, and
(c) at least one 4,4-diarylbutadiene compound; the weight ratio of the 4,4-diarylbutadiene compound to the dibenzoylmethane derivative being greater than 2.5 and said composition characteristically containing no cinnamate derivative.

This invention also relates to a process for improving the photostability of a 1,3,5-triazine derivative that is photosensitive in the presence of a UV-screening agent of the dibenzoylmethane derivative type, which entails formulating with the triazine derivative/dibenzoylmethane derivative combination an effective amount of at least one 4,4-diarylbutadiene compound.

2. Description of Background/Related/Prior Art

It is known that light radiation with wavelengths of between 280 nm and 400 nm permit tanning of the human epidermis and that light rays with wavelengths more particularly between 280 and 320 nm, known as UV-B rays, cause skin burns and erythema which can harm the development of a natural tan. For these reasons, as well as for aesthetic reasons, there is a constant demand for means of controlling this natural tanning in order thus to control the color of the skin; this UV-B radiation should thus be screened out.

It is also known that UV-A rays, with wavelengths between 320 and 400 nm, which cause browning of the skin, are liable to induce adverse changes therein, in particular in the case of sensitive skin or skin which is continually exposed to solar radiation. UV-A rays cause in particular a loss of elasticity of the skin and the appearance of wrinkles leading to premature aging of the skin. They promote triggering of the erythemal reaction or amplify this reaction in certain individuals and may even be the cause of phototoxic or photoallergic reactions. Thus, for aesthetic and cosmetic reasons such as the conservation of the skin's natural elasticity, for example, an increasingly large number of individuals wish to control the effect of UV-A rays on their skin. It is thus desirable also to screen out UV-A radiation.

In this respect, one particularly advantageous family of UV-A screening agents currently consists of dibenzoylmethane derivatives, and in particular 4-tert-butyl-4'-methoxydibenzoylmethane, which have high intrinsic absorbing power. These dibenzoylmethane derivatives, which are products which are now well known per se as screening agents that are active in the UV-A range, are described in particular in FR-A-2-326,405 and FR-A-2-440,933, as well as in EP-A-0-114,607; 4-tert-butyl-4'-methoxydibenzoylmethane is moreover currently sold under the trademark "Parsol 1789" by Hoffmann LaRoche.

1,3,5-Triazine derivatives are particularly desired in antisun cosmetics due to the fact that they are highly active in the UV-B range, and even in the UV-A range for some of these compounds depending on the nature of the substituents involved. They are especially described in patent applications U.S. Pat. No. 4,367,390, EP-863,145, EP-517,104, EP-570,838, EP-507,691, EP-796,851, EP-775,698, EP-878,469 and EP-933,376, and the following are known in particular:

2,4,6-tris[p-(2'-ethylhexyl-1'-oxycarbonyl)anilino]-1,3,5-triazine or "Ethylhexyl Triazone" (INCI name), sold under the trademark "Uvinul T 150" by BASF, 2-[(p-(tert-butylamido)anilino]-4,6-bis[(p-(2'-ethylhexyl-1'-oxycarbonyl)anilino]-1,3,5-triazine or "Diethylhexyl Butamido Triazone" (INCI name), sold under the trademark "Uvasorb HEB" by Sigma 3V. They have high UVB-absorbing power and it would therefore be very advantageous to be able to use them in combination with 4-tert-butyl-4'-methoxydibenzoylmethane mentioned above with the aim of obtaining products that afford broad and effective protection against all UV radiation.

EP-0-967,200, DE-197,46,654, DE-197,55,649, EP-1-008,586, DE-100,07,017, EP-1-133,980 and EP-1-133,981 disclose antisun compositions based on 4,4-diarylbutadienes, which may contain other additional screening agents, for instance the dibenzoylmethane derivatives and the triazine derivatives as mentioned above.

However, it has now been found that certain of these 1,3,5-triazine derivatives are photosensitive when they are in the presence of 4-tert-butyl-4'-methoxydibenzoylmethane, i.e., under UV irradiation, they have the drawback of undergoing substantial chemical degradation. Under these conditions, the combination of the two screening agents no longer affords prolonged, broad antisun protection to the skin and the hair.

SUMMARY OF THE INVENTION

After considerable research conducted in the field of photoprotection indicated above, it has now unexpectedly and surprisingly been determined that by introducing a 4,4-diarylbutadiene compound into a composition containing 4-tert-butyl-4'-methoxydibenzoylmethane in combination with at least one 1,3,5-triazine derivative that is photosensitive in the presence of the said dibenzoylmethane, the photostability of this 1,3,5-triazine derivative in such compositions, and thus the overall efficacy of these compositions, may be quite outstandingly improved.

This discovery is the basis of the present invention.

Thus, the present invention features cosmetic or dermatological compositions for topical application, in particular in a regime/regimen for photoprotecting the skin and the hair, comprising, formulated into a cosmetically acceptable support; at least one:

(a) a UV-screening dibenzoylmethane derivative,
(b) a UV-screening 1,3,5-triazine derivative that is photosensitive in the presence of a dibenzoylmethane derivative, and
(c) 4,4-diarylbutadiene compound; the weight ratio of the 4,4-diarylbutadiene compound to the dibenzoylmethane derivative being greater than 2.5 and said composition advantageously being devoid of any cinnamate sunscreen.

According to the present invention, cosmetic and/or dermatological compositions are produced containing 4-tert-butyl-4'-methoxydibenzoyl-methane in combination with at least one photosensitive 1,3,5-triazine derivative, in which compositions the concentration of 1,3,5-triazine derivative remains relatively constant even if these compositions are subjected to the action of light.

The present invention also features the use of a 4,4-diarylbutadiene compound for the manufacture of cosmetic or dermatological compositions containing a dibenzoylmethane derivative in combination with at least one photosensitive 1,3,5-triazine derivative, in order to improve the stability towards UV radiation (photostability) of the said 1,3,5-triazine derivative in such compositions.

This invention also features a process for improving the stability towards UV radiation (photostability) of a 1,3,5-triazine derivative that is photosensitive in the presence of a dibenzoylmethane derivative; the said process entailing adding to said combination an effective amount of a 4,4-diarylbutadiene compound.

DETAILED DESCRIPTION OF BEST MODE AND SPECIFIC/PREFERRED EMBODIMENTS OF THE INVENTION

In accordance with the invention, the expression "effective amount of 4,4-diarylbutadiene" means an amount that is sufficient to obtain an appreciable and significant improvement in the photostability of the 1,3,5-triazine derivative in the photoprotective cosmetic composition. This minimum amount of photostabilizing agent to be used, which may vary depending on the nature of the cosmetically acceptable support selected for the composition, may be determined without difficulty by means of a standard test for measuring photostability.

In accordance with the invention, the term "4,4-diarylbutadiene compound" means any molecule comprising at least one 4,4-diarylbutadiene chromophoric group. This molecule may be in the form of a simple compound, an oligomer or a polymer grafted in the chain with the chromophoric group.

Other characteristics, aspects, embodiments and advantages of the present invention will become apparent from the detailed description that follows.

A first compound of the compositions according to the invention is thus a 1,3,5-triazine derivative that is photosensitive in the presence of a dibenzoylmethane derivative.

Among the 1,3,5-triazine derivatives that may be used in the context of the present invention, it is especially preferred to use those corresponding to formula (I) below:

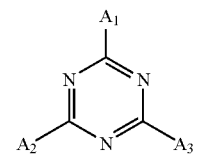

in which the radicals $A_1$, $A_2$ and $A_3$, which may be identical or different, are chosen from the groups of formula (II):

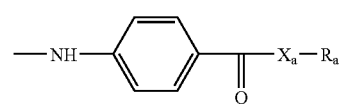

in which:
$X_a$, which may be identical or different, represents oxygen or —NH—;
$R_a$, which may be identical or different, is chosen from hydrogen, an alkali metal, an ammonium radical optionally substituted with one or more alkyl or hydroxyalkyl radicals, a linear or branched $C_1$–$C_{18}$ alkyl radical, a $C_5$–$C_{12}$ cycloalkyl radical optionally substituted with one or more $C_1$–$C_4$ alkyl radicals, a polyoxyethylenated radical comprising from 1 to 6 ethylene oxide units, the terminal OH group of which is methylated, a radical of formula (III), (IV) or (V) below:

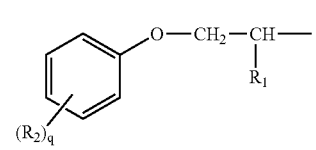

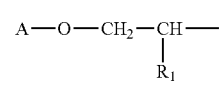

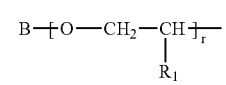

in which:
$R_1$ is hydrogen or a methyl radical;
$R_2$ is a $C_1$–$C_9$ alkyl radical;
q is an integer equal to 0 to 3;
r is an integer equal to 1 to 10;
A is a $C_4$–$C_8$ alkyl radical or a $C_5$–$C_8$ cycloalkyl radical;
B is chosen from: a linear or branched $C_1$–$C_8$ alkyl radical; a $C_5$–$C_8$ cycloalkyl radical; an aryl radical optionally substituted with one or more $C_1$–$C_4$ alkyl radicals.

A first family of 1,3,5-triazine derivatives that is more particularly preferred, and that is described especially in EP-A-0-517,104, is that of the 1,3,5-triazines corresponding to formula (I) in which $A_1$, $A_2$ and $A_3$ are of formula (II) and have the following characteristics:

one of the groups $X_a$—$R_a$ represents a radical —NH—$R_a$ with $R_a$ chosen from: a $C_5$–$C_{12}$ cycloalkyl radical optionally substituted with one or more $C_1$–$C_4$ alkyl radicals; a radical of formula (III), (IV) or (V) above in which:

B is a $C_1$–$C_4$ alkyl radical;

$R_2$ is a methyl radical;

the other two groups $X_a$—$R_a$ represent a radical —O—$R_a$ with $R_a$, which may be identical or different, chosen from: hydrogen; an alkali metal; an ammonium radical optionally substituted with one or more alkyl or hydroxyalkyl radicals; a linear or branched $C_1$–$C_{18}$ alkyl radical; a $C_5$–$C_{12}$ cycloalkyl radical optionally substituted with one or more $C_1$–$C_4$ alkyl radicals; a radical of formula (III), (IV) or (V) above in which:

B is a $C_1$–$C_4$ alkyl radical;

$R_2$ is a methyl radical.

A second family of 1,3,5-triazine derivatives that is more particularly preferred, and that is described especially in EP-A-0-570,838, is that of the 1,3,5-triazines corresponding to formula (I) in which $A_1$, $A_2$ and $A_3$ are of formula (II) and have all of the following characteristics:

one or two groups $X_a$—$R_a$ represent a radical —NH—$R_a$, with $R_a$ chosen from: a linear or branched $C_1$–$C_{18}$ alkyl radical; a $C_5$–$C_{12}$ cycloalkyl radical optionally substituted with one or more $C_1$–$C_4$ alkyl radicals; a radical of formula (III), (IV) or (V) above in which:

B is a $C_1$–$C_4$ alkyl radical;

$R_2$ is a methyl radical; the other or the other two group(s) $X_a$—$R_a$ being a radical —O—$R_a$ with $R_a$, which may be identical or different, chosen from: hydrogen; an alkali metal; an ammonium radical optionally substituted with one or more alkyl or hydroxyalkyl radicals; a linear or branched $C_1$–$C_{18}$ alkyl radical; a $C_5$–$C_{12}$ cycloalkyl radical optionally substituted with one or more $C_1$–$C_4$ alkyl radicals; a radical of formula (III), (IV) or (V) above in which:

B is a $C_1$–$C_4$ alkyl radical;

$R_2$ is a methyl radical.

A 1,3,5-triazine of this second family that is particularly preferred is 2-[(p-(tert-butylamido)-anilino]-4,6-bis[(p-(2'-ethylhexyl-1'-oxycarbonyl)-anilino]-1,3,5-triazine or "Diethylhexyl Butamido Triazone" sold under the trademark "Uvasorb HEB" by Sigma 3V and corresponding to the following formula:

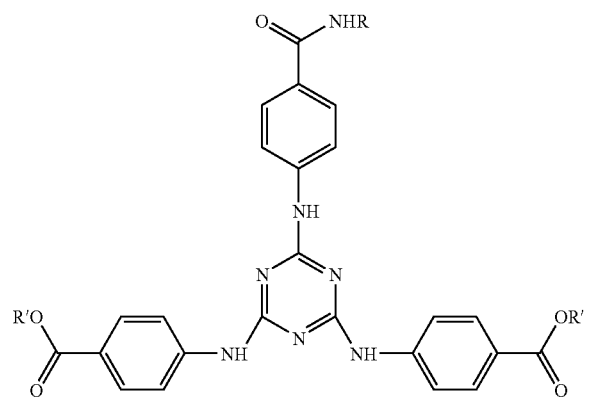

in which R' denotes a 2-ethylhexyl radical and R denotes a tert-butyl radical.

A third preferred family of compounds that may be used in the context of the present invention, and which is described especially in U.S. Pat. No. 4,724,137, is that of the 1,3,5-triazines corresponding to formula (I) in which $A_1$, $A_2$ and $A_3$ are of formula (II) and have the following characteristics:

$X_a$ are identical and represent oxygen;

$R_a$, which may be identical or different, represent a $C_6$–$C_{12}$ alkyl radical or a polyoxyethylenated radical comprising from 1 to 6 ethylene oxide units and in which the terminal OH group is methylated.

A 1,3,5-triazine of this third family that is particularly preferred is 2,4,6-tris[p(2'-ethylhexyl-1'-oxycarbonyl) anilino]-1,3,5-triazine or "Ethylhexyl Triazone" sold especially under the trademark "Uvinul T 150" by BASF and corresponds to the following formula:

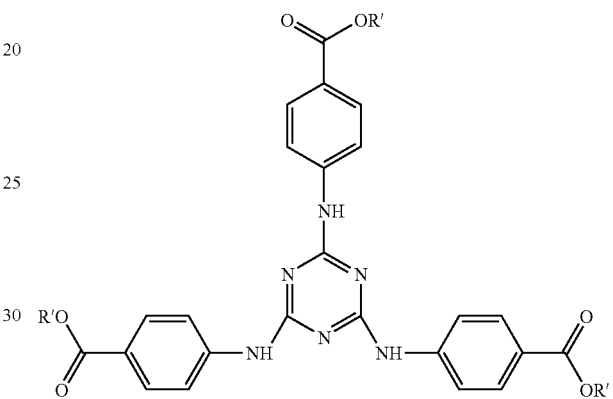

in which R' denotes a 2-ethylhexyl radical.

The 1,3,5-triazine derivative(s) is (are) generally present in the compositions of the invention in a content that can range from 0.5% to 15% and preferably from 1% to 10% by weight relative to the total weight of the composition.

A second compound of the compositions of the present invention is the dibenzoylmethane derivative. As mentioned above, the dibenzoylmethane derivatives of the present invention are products that are already well known per se and described in particular in the abovementioned documents FR-2-326,405, FR-2-440,933 and EP-0-114,607, the teachings of which documents are, as regards the actual definition of these products, entirely included as references in the present description. Among the dibenzoylmethane derivatives which are more particularly targeted by the present invention, mention may be made in particular, in a non-limiting manner, of:

2-methyldibenzoylmethane
4-methyldibenzoylmethane
4-isopropyldibenzoylmethane
4-tert-butyldibenzoylmethane
2,4-dimethyldibenzoylmethane
2,5-dimethyldibenzoylmethane
4,4'-diisopropyldibenzoylmethane
4-tert-butyl-4'-methoxydibenzoylmethane
2-methyl-5-isopropyl-4'-methoxydibenzoylmethane
2-methyl-5-tert-butyl-4'-methoxydibenzoylmethane
2,4-dimethyl-4'-methoxydibenzoylmethane
2,6-dimethyl-4-tert-butyl-4'-methoxydibenzoylmethane.

Among the dibenzoylmethane derivatives mentioned above, it is most particularly preferred to use, according to the present invention, 4-tert-butyl-4'-methoxydibenzoylmethane, in particular the product sold under the trademark "Parsol 1789" by Hoffmann LaRoche, this screening agent corresponding to the structural formula (VI) below:

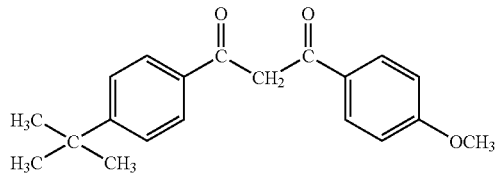

(VI)

Another dibenzoylmethane derivative which is preferred according to the present invention is 4-isopropyldibenzoylmethane, this screening agent being sold under the name "Eusolex 8020" by Merck and corresponding to the structural formula (VII) below:

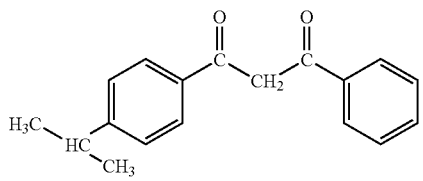

(VII)

The dibenzoylmethane derivative(s) may be present in the compositions in accordance with the invention in contents preferably ranging from 0.5% to 15% by weight and more preferably from 1% to 10% by weight, relative to the total weight of the composition.

Among the preferred 4,4-diarylbutadiene compounds in accordance with the invention that may be selected are the compounds corresponding to formula (VIII) below:

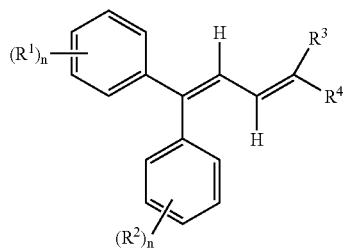

(VIII)

in which the diene system is of Z,Z; Z,E; E,Z or E,E configuration or mixtures of the said configurations, and in which:

$R_1$ and $R_2$, which may be identical or different, denote hydrogen, a linear or branched $C_1$–$C_{20}$ alkyl radical; a $C_2$–$C_{10}$ alkenyl radical; a $C_1$–$C_{12}$ alkoxy radical; a $C_3$–$C_{10}$ cycloalkyl radical; a $C_3$–$C_{10}$ cycloalkenyl radical; a linear or branched $C_1$–$C_{20}$ alkoxycarbonyl radical; a linear or branched $C_1$–$C_{12}$ monoalkylamino radical; a linear or branched $C_1$–$C_{12}$ dialkylamino radical; an aryl; a heteroaryl or a hydro-solubilizing substituent chosen from a carboxylate group, a sulfonate group and an ammonium residue;

$R^3$ denotes a group $COOR^5$; $COR^5$; $CONR^5R^6$; CN; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; a $C_6$–$C_{18}$ aryl radical; a $C_3$–$C_7$ heteroaryl radical;

$R^4$ denotes a group $COOR^6$; $COR^6$; $CONR^5R^6$; CN; a linear 20 or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; a heteroaryl radical;

$R^5$ and $R^6$, which may be identical or different, denote hydrogen; $[V]_o$—$R^7$; $C_1$–$C_6$-alkylene-$SO_3U$; $C_1$–$C_6$-alkylene-$PO_3U$; $C_1$–$C_6$-alkylene-$N(R^8)_3{}^+D^-$; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; a heteroaryl radical;

V denotes a group —$CH_2$—$CH_2$—W—, —$CH_2CH_2CH_2W$—, —$CH(CH_3)$—$CH_2$—W—, —$CH_2$—$CH_2$—$CH_2$—$CH_2$—W— or —$CH_2$—$CH(CH_2CH_3)$—W—;

D denotes Cl, Br, I or $SO_4R^9$;

U denotes hydrogen, $Na^+$, $K^+$, $Mg^{2+}$, $Ca^{2+}$, $Li^+$, $Al^{3+}$ or —$N(R^8)_4{}^+$;

W denotes O or NH;

$R^7$ and $R^8$, which may be identical or different, denote hydrogen, a linear or branched $C_1$–$C_6$ alkyl radical; a linear or branched $C_2$–$C_6$ alkenyl radical; a linear or branched $C_1$–$C_6$ acyl radical;

$R^9$ denotes hydrogen, a linear or branched $C_1$–$C_6$ alkyl radical; a $C_2$–$C_6$ alkenyl radical;

n ranges from 1 to 3;

o ranges from 0 to 150.

Examples of alkyl radicals that may be mentioned are: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Examples of $C_2$–$C_{10}$ alkenyl groups that may be mentioned are: ethenyl, n-propenyl, 1-methylethenyl, n-butenyl, 1-methylpropenyl, 2-methylpropenyl, 1,1-dimethylethenyl, n-pentenyl, 1-methylbutenyl, 2-methylbutenyl, 3-methylbutenyl, 2,2-dimethylpropenyl, 1-ethylpropenyl, n-hexenyl, 1,1-dimethylpropenyl, 1,2-dimethylpropenyl, 1-methylpentenyl, 2-methylpentenyl, 3-methylpentenyl, 4-methylpentenyl, 1,1-dimethylbutenyl, 1,2-dimethylbutenyl, 1,3-dimethylbutenyl, 2,2-dimethylbutenyl, 2,3-dimethylbutenyl, 3,3-dimethylbutenyl, 1-ethylbutenyl, 2-ethylbutenyl, 1,1,2-trimethyl-propenyl, 1,2,2-trimethylpropenyl, 1-ethyl-1-methyl-propenyl, 1-ethyl-2-methylpropenyl, n-heptenyl, n-octenyl, n-nonenyl, n-decenyl.

As $C_1$–$C_{12}$ alkoxy radicals for the radicals $R_1$ and $R_2$, mention may be made of: methoxy, n-propoxy, 1-methylethoxy, 1-methylpropoxy, n-pentoxy, 3-methylbutoxy, 2,2-dimethylpropoxy, 1-methyl-1-ethylpropoxy, octoxy, ethoxy, n-propoxy, n-butoxy, 2-methylpropoxy, 1,1-dimethylpropoxy, hexoxy, heptoxy, 2-ethylhexoxy.

Examples of $C_3$–$C_{10}$ cycloalkyl radicals which may be mentioned for the radicals $R^6$ and $R^7$ are: cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

As $C_3$–$C_{10}$ cycloalkenyl radicals containing one or more double bonds, for the radicals $R^6$ and $R^7$, mention may be made of: cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkyl or cycloalkenyl radicals may comprise one or more (preferably from 1 to 3) substituents chosen, for example, from halogen, for instance chlorine, fluorine or bromine; cyano; nitro; amino; $C_1$–$C_4$ alkylamino; $C_1$–$C_4$ dialkylamino; $C_1$–$C_4$ alkyl; $C_1$–$C_4$ alkoxy; hydroxyl; they may also comprise from 1 to 3 hetero atoms, for instance sulfur, oxygen or nitrogen, the free valencies of which may be satisfied with a hydrogen or a $C_1$–$C_4$ alkyl radical.

Examples of acyl radicals that may be mentioned include formyl, acetyl, propionyl and n-butyryl.

The bicycloalkyl or bicycloalkenyl groups are chosen, for example, from bicyclic terpenes, for instance pinane, bornane, pinene, camphor or adamantane derivatives.

The aryl groups are preferably chosen from phenyl and naphthyl rings, which may contain one or more (preferably, from 1 to 3) substituents chosen, for example, from halogen, for instance chlorine, fluorine or bromine; cyano; nitro; amino; $C_1$–$C_4$ alkylamino; $C_1$–$C_4$ dialkylamino; $C_1$–$C_4$ alkyl; $C_1$–$C_4$ alkoxy; hydroxyl. Phenyl, methoxyphenyl and naphthyl are more particularly preferred.

The heteroaryl groups generally comprise one or more hetero atoms chosen from sulfur, oxygen and nitrogen.

The hydro-solubilizing groups are, for example, carboxylate or sulfonate groups and more particularly salts thereof with physiologically acceptable cations, for instance the alkali metal salts or trialkylammonium salts such as the tris(hydroxyalkyl)ammonium or 2-methyl-1-propanol-2-ammonium salts. Mention may also be made of ammonium groups, for instance alkylammoniums and forms thereof salified with physiologically acceptable anions.

The preferred compounds of formula (VIII) are chosen from those of formula (VIIIa) below:

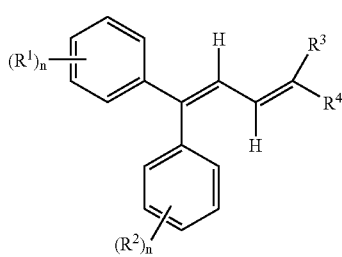

(VIIIa)

in which the diene system is of Z,Z; Z,E; E,Z or E,E configuration or mixtures of the said configurations, and in which:

$R^1$ and $R^2$, which may be identical or different, denote hydrogen, a $C_1$–$C_8$ alkyl radical; a $C_1$–$C_8$ alkoxy radical; a hydro-solubilizing substituent chosen from a carboxylate group, a sulfonate group and an ammonium residue;

$R^3$ denotes a group $COOR^5$; $CONR^5R^6$; $CN$;

$R^4$ denotes a group $COOR^6$; $CONR^5R^6$;

$R^5$ denotes hydrogen; $[V]_o$—$R^7$; $C_1$–$C_6$ alkylene-$SO_3U$; $C_1$–$C_6$ alkylene-$N(R^8)_3{}^+D^-$;

$R^6$ denotes $[V]_o$—$R^7$; $C_1$–$C_6$-alkylene-$SO_3U$; $C_1$–$C_6$ alkylene-$N(R^8)_3{}^+D^-$;

V denotes a —$CH_2$—$CH_2$—O—, —$CH_2CH_2CH_2O$—, —$CH(CH_3)$—$CH_2$—O— group;

D denotes Cl, Br, I or $SO_4R^9$;

U denotes hydrogen, $Na^+$, $K^+$, $Mg^{2+}$, $Ca^{2+}$, $Li^+$, $Al^{3+}$ or —$N(R^8)_4{}^-$ $R^7$, $R^8$ and $R^9$, which may be identical or different, denote hydrogen or a linear or branched $C_1$–$C_3$ alkyl radical;

n ranges from 1 to 3;

o ranges from 0 to 50.

The compounds of formula (VIII) that are even more preferred are chosen from those corresponding to formula (VIIIb) below:

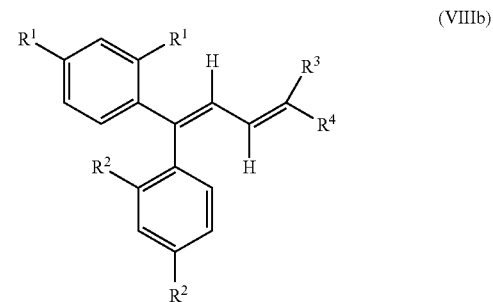

(VIIIb)

in which the diene system is of Z,Z; Z,E; E,Z or E,E configuration or mixtures of the said configurations, and in which:

$R^1$ and $R^2$, which may be identical or different, denote hydrogen, a $C_1$–$C_8$ alkyl radical; a $C_1$–$C_8$ alkoxy radical;

$R^3$ denotes a group $COOR^5$; $CONR^5R^6$; $CN$;

$R^4$ denotes a group $COOR^6$; $CONR^5R^6$;

$R^5$ denotes hydrogen; $[V]_o$—$R^7$; $C_1$–$C_6$-alkylene-$SO_3U$; $C_1$–$C_6$-alkylene-$N(R^8)_3{}^+D^-$;

$R^6$ denotes $[V]_o$—$R^7$; $C_1$–$C_6$-alkylene-$SO_3U$; $C_1$–$C_6$-alkylene-$N(R^8)_3{}^+D^-$;

V denotes a —$CH_2$—$CH_2$—O—, —$CH_2CH_2CH_2O$—, —$CH(CH_3)$—$CH_2$—O— group;

D denotes Cl, Br, I or $SO_4R^9$;

U denotes hydrogen, $Na^+$, $K^+$, $Mg^{2+}$, $Ca^{2+}$, $Li^+$, $Al^{3+}$ or —$N(R^8)_4{}^+$ $R^7$, $R^8$ and $R^9$, which may be identical or different, denote hydrogen or a linear or branched $C_1$–$C_3$ alkyl radical;

o ranges from 0 to 50.

The compounds of formula (VIII) that are even more preferred are chosen from those corresponding to formula (VIIIc) below:

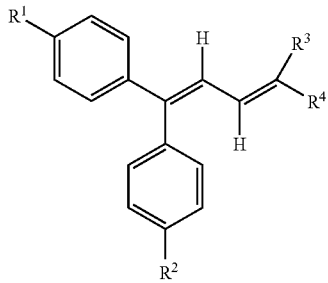

(VIIIc)

in which the diene system is of Z,Z; Z,E; E,Z or E,E configuration or mixtures of the said configurations, and in which:

R¹ and R², which may be identical or different, denote hydrogen, a $C_1$–$C_8$ alkyl radical; a $C_1$–$C_8$ alkoxy radical;

R³ denotes a group $COOR^5$; $CONR^5R^6$; CN;

R⁴ denotes a group $COOR^6$; $CONR^5R^6$;

R⁵ denotes hydrogen; $[X]_p$—R⁷; $C_1$–$C_6$-alkylene-$SO_3Y$; $C_1$–$C_6$-alkylene-$N(R^8)_3^+D^-$;

R⁶ denotes $[V]_o$—R⁷; $C_1$–$C_6$-alkylene-$SO_3U$; $C_1$–$C_6$-alkylene-$N(R^8)_3^-D^-$;

V denotes a —$CH_2$—$CH_2$—O—, —$CH_2CH_2CH_2O$—, —$CH(CH_3)$—$CH_2$—O— group

D denotes Cl, Br, I or $SO_4R^9$;

U denotes hydrogen, $Na^+$, $K^+$, $Mg^{2+}$, $Ca^{2+}$, $Li^+$, $Al^{3+}$ or —$N(R^8)_4^+$ R⁷, R⁸ and R⁹, which may be identical or different, denote hydrogen or a linear or branched $C_1$–$C_3$ alkyl radical;

o ranges from 0 to 50.

The compounds of formula (VIII) that are even more particularly preferred are chosen from the following compounds:

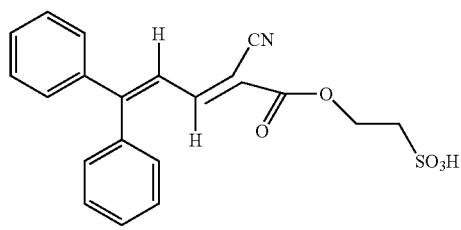

(6)

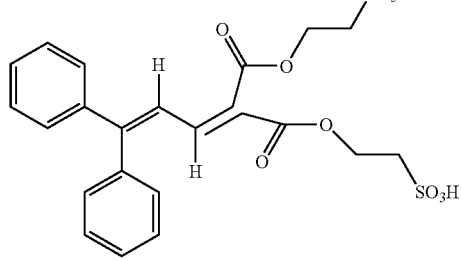

(7)

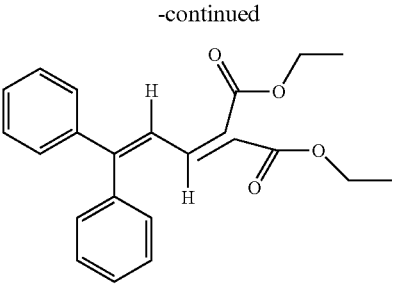

(8)

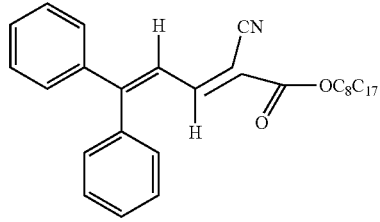

(9)

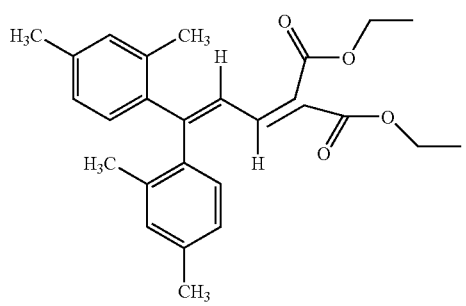

(10)

The compounds of formula (VIII) as defined above are known per se and their structures and syntheses are described in patent applications EP-0-967,200, DE-197-46,654 and DE-197-55,649 (which form an integral part of the content of the description).

Among the preferred 4,4-diarylbutadiene compounds in accordance with the invention that may also be mentioned are the oligomers corresponding to formula (IX) below:

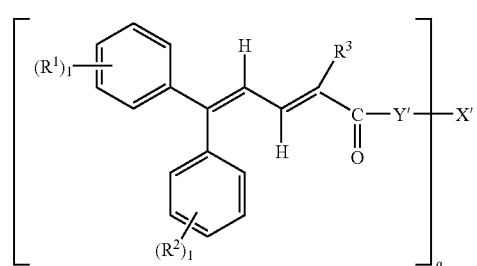

(IX)

in which the diene system is of Z,Z; Z,E; E,Z or E,E configuration or mixtures of the said configurations, and in which:

R¹, R², R³ and I have the same definitions as in formula (VIII) above;

Y' denotes a group —O— or —$NR^{10}$—;

R¹⁰ denotes hydrogen; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl; a heteroaryl;

X' denotes an aliphatic or cycloaliphatic linear or branched polyol residue comprising from 2 to 10 hydroxyl groups and of valency q; the carbon-based chain of the said residue possibly being interrupted with one or more sulfur or oxygen atoms; one or more imine groups; one or more $C_1$–$C_4$ alkylimino groups;

q ranges from 2 to 10.

X' is a polyol residue containing from 2 to 10 hydroxyl groups and especially:

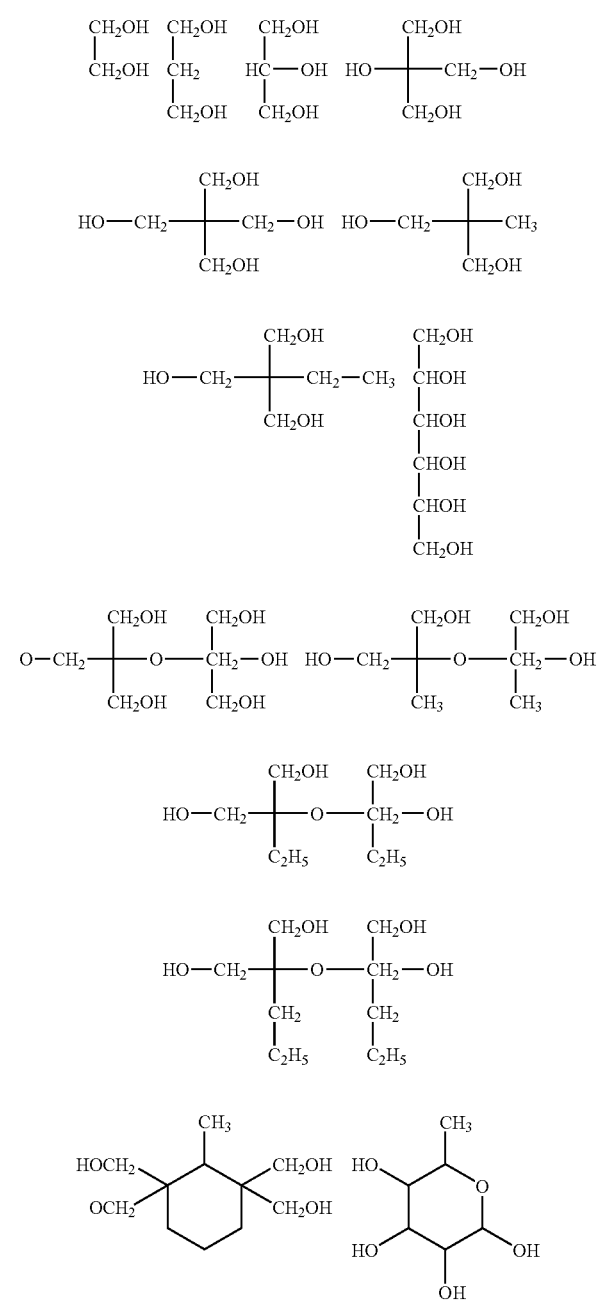

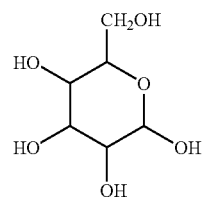

-continued

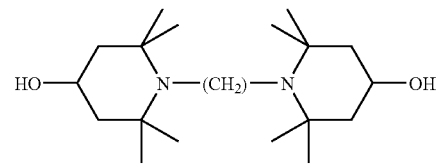

The compounds of formula (IX) that are more preferred are those for which:

$R^1$ and $R^2$, which may be identical or different, denote hydrogen, a $C_1$–$C_{12}$ alkyl radical; a $C_1$–$C_8$ alkoxy radical; a hydro-solubilizing substituent chosen from a carboxylate group, a sulfonate group and an ammonium residue;

$R^3$ denotes a group $COOR^5$; $CONR^5R^6$; CN; a $C_3$–$C_{10}$ cycloalkyl radical; a $C_7$–$C_{10}$ bicycloalkyl radical;

$R^5$ and $R^6$, which may be identical or different, denote a linear or branched $C_1$–$C_{20}$ alkyl radical; a $C_3$–$C_{10}$ cycloalkyl radical; a $C_7$–$C_{10}$ bicycloalkyl radical; optionally substituted naphthyl or phenyl;

X' denotes a polyol residue comprising from 2 to 6 and more particularly from 2 to 4 hydroxyl groups.

The compounds of formula (IX) that are even more preferred are those for which:

X' denotes an ethanol or pentaerythrol residue.

The compounds of formula (IX) that are even more particularly preferred are chosen from the following compounds:

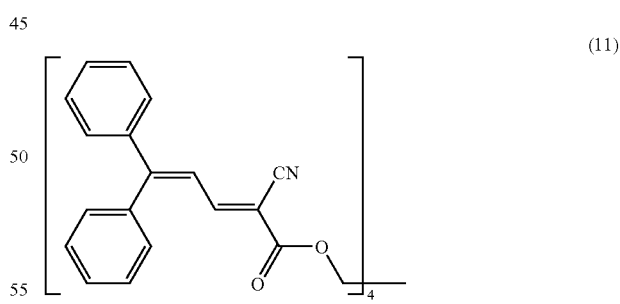

(11)

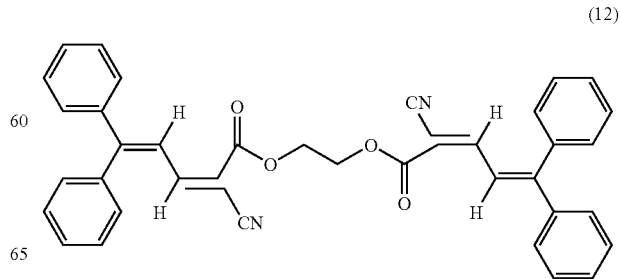

(12)

-continued (13)

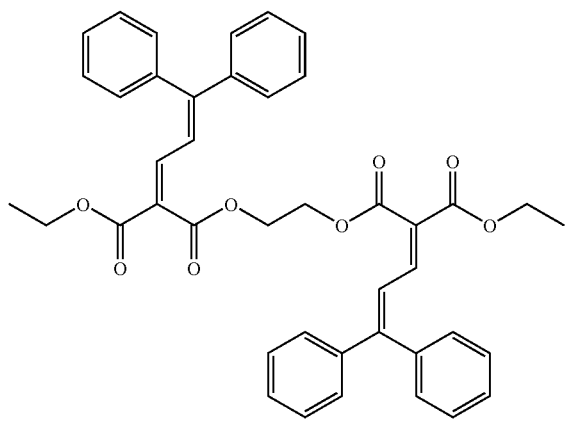

The compounds of formula (IX) as defined above are known per se and their structures and syntheses are described in EP-A-1-008,586 (which forms an integral part of the content of the description).

The 4,4-diarylbutadiene compounds in accordance with the invention are present in the composition of the invention in contents preferably ranging from 0.5% to 15% by weight and more preferably from 1% to 10% by weight, relative to the total weight of the composition.

The compositions in accordance with the invention may also comprise other additional organic UV-screening agents that are active in the UVA and/or UVB range (absorbers), which are water-soluble or liposoluble or even insoluble in the cosmetic solvents commonly used.

The additional organic UV-screening agents are especially chosen from anthranilates; salicylic derivatives; camphor derivatives; benzophenone derivatives; β,β-diphenylacrylate derivatives; benzotriazole derivatives; non-photosensitive triazine derivatives; benzalmalonate derivatives; benzimidazole derivatives; imidazolines; bis-benzazolyl derivatives as described in EP-669,323 and U.S. Pat. No. 2,463,264; p-aminobenzoic acid (PABA) derivatives; methylenebis(hydroxyphenyl)benzotriazole derivatives as described in U.S. Pat. Nos. 5,237,071, 5,166,355, GB-2-303,549, DE-197-26,184 and EP-893,119; screening polymers and screening silicones such as those described especially in WO 93/04665; dimers derived from α-alkylstyrene, such as those described in DE-198-55,649.

As examples of additional UV-A-active and/or UV-B-active organic screening agents, mention may be made of the following, denoted hereinbelow under their INCI name:

para-Aminobenzoic Acid Derivatives:
PABA,
Ethyl PABA,
Ethyl dihydroxypropyl PABA,
Ethylhexyl dimethyl PABA sold in particular under the name "Escalol 507" by ISP,
Glyceryl PABA,
PEG-25 PABA sold under the name "Uvinul P25" by BASF
Salicylic Derivatives:
Homosalate sold under the name "Eusolex HMS" by Rona/EM Industries,
Ethylhexyl salicylate sold under the name "Neo 10 Heliopan OS" by Haarmann and Reimer,
Dipropylene glycol salicylate sold under the name "Dipsal" by Scher,
TEA salicylate sold under the name "Neo Heliopan TS" by Haarmann and Reimer.
β,β-Diphenyl Acrylate Derivatives:
Octocrylene sold in particular under the trademark "Uvinul N539" by BASF
Etocrylene sold in particular under the trademark "Uvinal N35" by BASF
Benzophenone Derivatives:
Benzophenone-1 sold under the trademark "Uvinul 400" by BASF,
Benzophenone-2 sold under the trademark "Uvinul D50" by BASF,
Benzophenone-3 or Oxybenzone sold under the trademark "Uvinul M40" by BASF,
Benzophenone-4 sold under the trademark "Uvinul MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "Uvinul DS-49" by BASF,
Benzophenone-12.
Benzylidenecamphor Derivatives:
3-Benzylidenecamphor manufactured under the name "Mexoryl SD" by Chimex,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.
Benzimidazole Derivatives:
Phenylbenzimidazolesulfonic acid sold in particular under the trademark "Eusolex 232" by Merck,
Benzimidazilate sold under the trademark "Neo Heliopan AP" by Haarmann and Reimer.
Triazine Derivatives:
Anisotriazine sold under the trademark "Tinosorb S" by Ciba Specialty Chemicals
2,4,6-tris(Diisobutyl 4'-aminobenzmalonate) s-triazine.
Benzotriazole Derivatives:
Drometrizole trisiloxane sold under the name "Silatrizole" by Rhodia Chimie,
Methylenebis(benzotriazolyl)tetramethylbutylphenol sold in solid form under the trademark "MIXXIM BB/100" by Fairmount Chemical, or in micronized form as an aqueous dispersion under the trademark "Tinosorb M" by Ciba Specialty Chemicals.
Anthranilic Derivatives:
Menthyl anthranilate sold under the trademark "Neo Heliopan MA" by Haarmann and Reimer.
Imidazoline Derivatives:
Ethylhexyldimethoxybenzylidenedioxoimidazoline propionate.
Benzalmalonate Derivatives:
Polyorganosiloxane containing benzalmalonate functions, sold under the trademark "Parsol SLX" by Hoffmann LaRoche and mixtures thereof.

The organic UV-screening agents that are more particularly preferred are chosen from the following compounds:

Ethylhexyl salicylate,
Octocrylene,
Phenylbenzimidazolesulfonic acid,
Benzophenone-3,
Benzophenone-4,
Benzophenone-5,
4-Methylbenzylidenecamphor,
Terephthalylidenedicamphorsulfonic acid,
Disodium phenyl dibenzimidazole tetrasulfonate,
2,4,6-tris(Diisobutyl 4'-aminobenzalmalonate)-s-triazine,
Anisotriazine,
Methylenebis(benzotriazolyl)tetramethylbutyl-phenol,
Drometrizole trisiloxane, and mixtures thereof.

The cosmetic compositions according to the invention may also comprise pigments or nanopigments (average size of the primary particles: generally between 5 nm and 100 nm and preferably between 10 nm and 50 nm) of coated or uncoated metal oxides, such as, for example, nanopigments of titanium oxide (amorphous or crystallized in rutile and/or anatase form), of iron oxide, of zinc oxide, of zirconium oxide or of cerium oxide, which are all UV photoprotective agents that are well known per se. Standard coating agents are, moreover, alumina and/or aluminum stearate. Such coated or uncoated metal oxide nanopigments are described in particular in EP-A-0-518,772 and EP-A-0-518,773.

The compositions according to the invention may also contain agents for artificially tanning and/or browning the skin (self-tanning agents) such as, for example, dihydroxyacetone (DHA).

The compositions of the invention may also comprise standard cosmetic adjuvants chosen especially from fatty substances, organic solvents, ionic or nonionic thickeners, softeners, antioxidants, free-radical scavengers, opacifiers, stabilizers, emollients, silicones, α-hydroxy acids, antifoams, moisturizers, vitamins, insect repellants, fragrances, preserving agents, surfactants, anti-inflammatories, substance P antagonists, fillers, polymers, acidifying or basifying agents, colorants or any other ingredient usually used in cosmetics, in particular for the manufacture of antisun compositions in the form of emulsions.

The fatty substances may consist of an oil or a wax or mixtures thereof. The term "oil" means a compound that is liquid at room temperature. The term "wax" means a compound that is solid or substantially solid at room temperature, and whose melting point is generally above 35° C. They also comprise linear or cyclic fatty acids, fatty alcohols and fatty acid esters such as benzoic acid, trimellitic acid and hydroxybenzoic acid derivatives.

Oils that may be mentioned include mineral oils (paraffin); plant oils (sweet almond oil, macadamia oil, blackcurrant pip oil or jojoba oil); synthetic oils, for instance perhydrosqualene, fatty alcohols, fatty acids or fatty esters (for instance the $C_{12}$–$C_{15}$ alkyl benzoates sold under the trademark "Finsolv TN" by Finetex, octyl palmitate, isopropyl lanolate, triglycerides including capric/caprylic acid triglycerides), oxyethylenated or oxypropylenated fatty esters and ethers; silicone oils (cyclomethicone, and polydimethylsiloxanes or PDMS) or fluoro oils, and polyalkylenes.

Waxy compounds that may be mentioned include paraffin, carnauba wax, beeswax and hydrogenated castor oil.

Among the organic solvents that may be mentioned are lower alcohols and polyols.

Needless to say, a person skilled in the art will take care to select this or these optional additional compound(s) and/or the amounts thereof such that the advantageous properties, in particular the photostability of the triazine derivative, intrinsically associated with the compositions in accordance with the invention are not, or are not substantially, adversely affected by the envisaged addition(s).

The compositions of the invention may be prepared according to techniques that are well known to those skilled in the art, in particular those intended for preparing emulsions of oil-in-water or water-in-oil type.

These compositions may be in particular in the form of a simple emulsion or a complex emulsion (O/W, W/O, O/W/O or W/O/W), such as a cream, a milk, a gel or a cream-gel; a powder or a solid tube, and may optionally be packaged as an aerosol and may be in the form of a mousse or spray.

When it is an emulsion, the aqueous phase of this emulsion may comprise a nonionic vesicular dispersion prepared according to known processes (Bangham, Standish and Watkins, J. Mol. Biol. 13, 238 (1965), FR-2-315,991 and FR-2-416,008).

The cosmetic composition of the invention may be used as a composition for protecting the human epidermis or the hair against ultraviolet rays, as an antisun composition or as a makeup product.

When the cosmetic composition according to the invention is used in a regime or regimen for protecting the human epidermis against UV rays, or as an antisun composition, it may be in the form of a suspension or a dispersion in solvents or fatty substances, in the form of a nonionic vesicular dispersion or in the form of an emulsion, preferably of oil-in-water type, such as a milk or a cream, or in the form of an ointment, a gel, a cream-gel, a solid tube, a powder, a stick, an aerosol mousse or a spray.

When the cosmetic composition according to the invention is used for protecting the hair against UV rays, it may be in the form of a shampoo, a lotion, a gel, an emulsion or a nonionic vesicular dispersion and may constitute, for example, a rinse-out composition, to be applied before or after shampooing, before or after dyeing or bleaching, or before, during or after permanent-waving or straightening the hair, a styling or treating lotion or gel, a blow-drying or hairsetting lotion or gel, or a permanent-waving, straightening, dyeing or bleaching composition for the hair.

When the composition is used as a makeup product for the eyelashes, the eyebrows or the skin, such as an epidermal treatment cream, a foundation, a tube of lipstick, an eyeshadow, a face powder, mascara or an eyeliner, it may be in solid or pasty, anhydrous or aqueous form, for instance oil-in-water or water-in-oil emulsions, nonionic vesicular dispersions or suspensions.

As a guide, for the antisun formulations in accordance with the invention that contain a support of oil-in-water emulsion type, the aqueous phase (especially comprising the hydrophilic screening agents) generally represents from 50% to 95% by weight and preferably from 70% to 90% by weight, relative to the total weight of the formulation, the oily phase (especially comprising the lipophilic screening agents) from 5% to 50% by weight and preferably from 10% to 30% by weight, relative to the total weight of the formulation, and the (co)emulsifier(s) from 0.5% to 20% by weight and preferably from 2% to 10% by weight, relative to the total weight of the formulation.

As indicated above, the present invention features the use of a composition as defined above for the manufacture of a cosmetic or dermatological composition intended for protecting the skin and/or the hair against ultraviolet radiation, in particular solar radiation.

In order to further illustrate the present invention and the advantages thereof, the following specific examples are given, it being understood that same are intended only as illustrative and in nowise limitative. In said examples to follow, all parts and percentages are given by weight, unless otherwise indicated.

The following Tables 1 and report Examples 1 and 2, specific compositions according to the invention.

TABLE 1

| COMPOSITION | EXAMPLE 1 |
|---|---|
| Glyceryl mono/distearate/polyethylene glycol stearate (100 EO) mixture (Arlacel 165 FL - ICI) | 2 |
| Stearyl alcohol (Lanette 18 - Henkel) | 1 |
| Stearic acid from palm oil (Stearine TP - Stearinerie Dubois) | 2.5 |
| Polydimethylsiloxane (Dow Corning 200 Fluid - Dow Corning) | 0.5 |
| C12/C15 alkyl benzoate (Witconol TN - WITCO) | 20 |
| Triethanolamine | 0.5 |
| Butylmethoxydibenzoylmethane (Parsol 1789 - Hoffmann LaRoche) | 2 |
| Ethylhexyl triazone (Uvinul T150, BASF) | 5 |
| Compound of formula (6) | 8 |
| Glycerol | 4 |
| Triethanolamine | 0.3 |
| Polyacrylic acid (Synthalen K - 3 V) | 0.4 |
| Preserving agents | qs |
| Demineralized water | 100 g |

TABLE 2

| COMPOSITION | EXAMPLE 2 |
|---|---|
| 80/20 mixture of cetylstearyl alcohol and of oxyethylenated (33 EO) cetylstearyl alcohol (Sinnowax AO - Henkel) | 7 |
| Mixture of glyceryl mono- and distearate (Cerasynt SD-V ISP) | 2 |
| Cetyl alcohol | 1.5 |
| Polydimethylsiloxane (Dow Corning 200 fluid - Dow Corning) | 1.5 |
| Liquid petroleum jelly | 15 |
| Butylmethoxydibenzoylmethane (Parsol 1789 - Hoffmann LaRoche) | 2 |
| Compound of formula (II) | 6 |
| Ethylhexyl triazone (Uvinul T150, BASF) | 5 |
| Glycerol | 15 |
| Preserving agents | qs |
| Demineralized water | 100 g |

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, photostable cosmetic/dermatological UV-screening composition suited for photoprotecting the skin and the hair, comprising:
    (a) at least one UV-screening dibenzoylmethane compound,
    (b) at least one UV-screening 1,3,5-triazine compound that is photosensitive in the presence of a dibenzoylmethane compound, and
    (c) a 1,3,5-triazine photostabilizing amount of at least one 4,4-diarylbutadiene compound, formulated into a topically applicable, cosmetically/dermatologically acceptable support therefor.

2. The photostable cosmetic/dermatological composition as defined by claim 1, the weight ratio of said at least one diarylbutadiene compound to said at least one dibenzoylmethane compound being greater than 2.5 and said composition being devoid of any cinnamate sunscreen.

3. The photostable cosmetic/dermatological composition as defined by claim 1, said at least one 1,3,5-triazine compound having the formula (I) below:

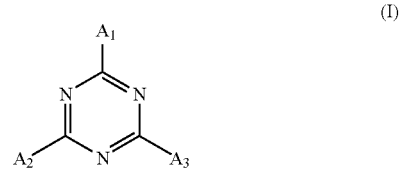

in which the radicals $A_1$, $A_2$ and $A_3$, which may be identical or different, are each a radical of formula (II):

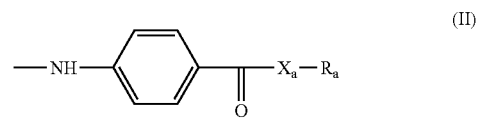

in which the radicals $X_a$, which may be identical or different, are each oxygen or a radical —NH—; the radials $R_a$, which may be identical or different, are chosen from hydrogen; an alkali metal; an ammonium radical optionally substituted with one or more alkyl or hydroxyalkyl radicals; a linear or branched $C_1$–$C_{18}$ alkyl radical; a $C_5$–$C_{12}$ cycloalkyl radical optionally substituted with one or more $C_1$–$C_4$ alkyl radicals; a polyoxyethylenated radical comprising from 1 to 6 ethylene oxide units, the terminal OH group of which is methylated; a radical of formula (III), (IV) or (V) below:

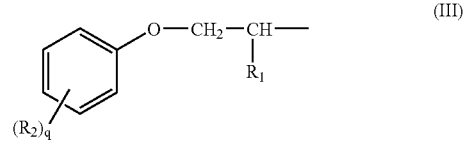

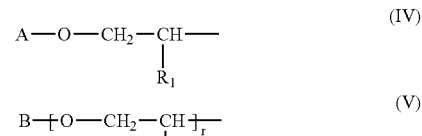

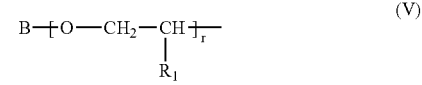

in which $R_1$ is hydrogen or a methyl radical; $R_2$ is a $C_1$–$C_9$ alkyl radical; q is an integer ranging from 0 to 3; r is an integer ranging from 1 to 10; A is a $C_4$–$C_8$ alkyl radical or a $C_5$–$C_8$ cycloalkyl radical; and B is a linear or branched $C_1$–$C_8$ alkyl radical; a $C_5$–$C_8$ cycloalkyl radical; an aryl radical optionally substituted with one or more $C_1$–$C_4$ alkyl radicals.

4. The photostable cosmetic/dermatological composition as defined by claim 3, wherein said 1,3,5-triazine compound of formula (I), A₁, A₂ and A₃ have the formula (II) and one of the groups $X_a$—$R_a$ is a radical —NH—$R_a$ wherein $R_a$ is a $C_5$–$C_{12}$ cycloalkyl radical optionally substituted with one or more $C_1$–$C_4$ alkyl radicals; a radical of formula (III), (IV) or (V) above in which B is a $C_1$–$C_4$ alkyl radical; $R_2$ is a methyl radical; the other two groups $X_a$—$R_a$ are a radical —O—$R_a$ with the radicals $R_a$, which may be identical or different, chosen from: hydrogen; an alkali metal; an ammonium radical optionally substituted with one or more alkyl or hydroxyalkyl radicals; a linear or branched $C_1$–$C_{18}$ alkyl radical; a $C_5$–$C_{12}$ cycloalkyl radical optionally substituted with one or more $C_1$–$C_4$ alkyl radicals; a radical of formula (III), (IV) or (V) above in which B is a $C_1$–$C_4$ alkyl radical; $R_2$ is a methyl radical.

5. The photostable cosmetic/dermatological composition as defined by claim 3, wherein said 1,3,5-triazine compound, A₁, A₂ and A₃ are of formula (II) and have all of the following characteristics: one or two groups $X_a$—$R_a$ represent a radical —NH—$R_a$, wherein $R_a$ is a linear or branched $C_1$–$C_{18}$ alkyl radical; a $C_5$–$C_{12}$ cycloalkyl radical optionally substituted with one or more $C_1$–$C_4$ alkyl radicals; a radical of formula (III), (IV) or (V) above in which B is a $C_1$–$C_4$ alkyl radical; $R_2$ is a methyl radical; the other or the other two group(s) $X_a$—$R_a$ being a radical —O—$R_a$ wherein the radicals $R_a$, which may be identical or different, are each hydrogen; an alkali metal; an ammonium radical optionally substituted with one or more alkyl or hydroxyalkyl radicals; a linear or branched $C_1$–$C_{18}$ alkyl radical; a $C_5$–$C_{12}$ cycloalkyl radical optionally substituted with one or more $C_1$–$C_4$ alkyl radicals; a radical of formula (III), (IV) or (V) above in which B is a $C_1$–$C_4$ alkyl radical; and $R_2$ is a methyl radical.

6. The photostable cosmetic/dermatological composition as defined by claim 5, said at least one 1,3,5-triazine compound having the following formula:

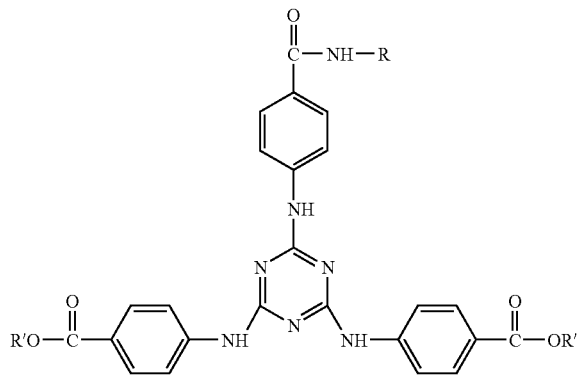

in which R' is a 2-ethylhexyl radical and R is a tert-butyl radical.

7. The photostable cosmetic/dermatological composition as defined by claim 3, wherein said 1,3,5-triazine compound of formula (I), A₁, A₂ and A₃ are of formula (II) and have the following characteristics: the radicals $X_a$ are identical and represent oxygen; the radicals $R_a$, which may be identical or different, are each a $C_6$–$C_{12}$ alkyl radical or a polyoxyethylenated radical comprising from 1 to 6 ethylene oxide units and in which the terminal OH group is methylated.

8. The photostable cosmetic/dermatological composition as defined by claim 7, said at least one 1,3,5-triazine compound having the following formula:

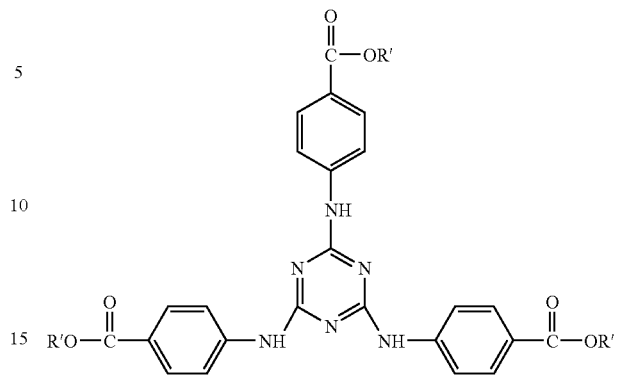

in which R' is a 2-ethylhexyl radical.

9. The photostable cosmetic/dermatological composition as defined by claim 1, said at least one 1,3,5-triazine compound comprising from 0.5% to 15% by weight thereof.

10. The photostable cosmetic/dermatological composition as defined by claim 1, said at least one dibenzoylmethane compound being selected from the group consisting of:
 2-methyldibenzoylmethane,
 4-methyldibenzoylmethane
 4-isopropyldibenzoylmethane
 4-tert-butyldibenzoylmethane
 2,4-dimethyldibenzoylmethane,
 2,5-dimethyldibenzoylmethane,
 4,4'-diisopropyldibenzoylmethane,
 4,4'-dimethoxydibenzolymethane,
 4-tert-butyl-4'-methoxydibenzoylmethane,
 2-methyl-5-isopropyl-4'-methoxydibenzoylmethane,
 2-methyl-5-tert-butyl-4'-methoxydibenzoylmethane,
 2,4-dimethyl-4'-methoxydibenzoylmethane,
 2,6-dimethyl-4-tert-butyl-4'-methoxydibenzoyl-methane,
 and mixtures thereof.

11. The photostable cosmetic/dermatological composition as defined by claim 10, said at least one dibenzoylmethane compound comprising 4-tert-butyl-4'-methoxydibenzoylmethane.

12. The photostable cosmetic/dermatological composition as defined by claim 10, said at least one dibenzoylmethane compound comprising 4-isopropyldibenzoylmethane.

13. The photostable cosmetic/dermatological composition as defined by claim 1, said at least one dibenzoylmethane compound comprising from 0.5% to 15% by weight thereof.

14. The photostable cosmetic/dermatological composition as defined by claim 1, said at least one 4,4-diarylbutadiene compound having the formula (VIII) below:

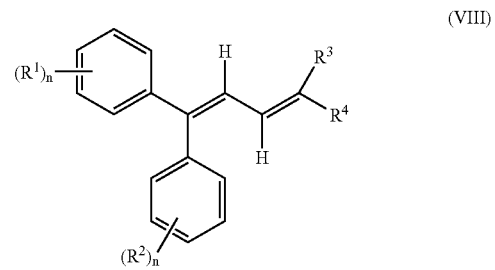

(VIII)

in which the diene system is of Z,Z; Z,E; E,Z or E,E configuration or mixtures of the said configurations, and in which the radicals $R^1$ and $R^2$, which may be identical or different, are each hydrogen, a linear or branched $C_1$–$C_{20}$ alkyl radical; a $C_2$–$C_{10}$ alkenyl radical; a $C_1$–$C_{12}$ alkoxy radical; a $C_3$–$C_{10}$ cycloalkyl radical; a $C_3$–$C_{10}$ cycloalkenyl radical; a linear or branched $C_1$–$C_{20}$ alkoxycarbonyl radical; a linear or branched $C_1$–$C_{12}$ monoalkylamino radical; a linear or branched $C_1$–$C_{12}$ dialkylamino radical; an aryl radical; a heteroaryl radical or a hydro-solubilizing substituent which comprises a carboxylate group, a sulfonate group or an ammonium residue; $R^3$ is a group $COOR^5$; $COR^5$; $CONR^5R^6$; CN; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; a $C_6$–$C_{18}$ aryl radical; a $C_3$–$C_7$ heteroaryl radical; $R^4$ is a group $COOR^6$; $COR^6$; $CONR^5R^6$; CN; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; a heteroaryl radical; the radicals $R^5$ and $R^6$, which may be identical or different, are each hydrogen; $[V]_o$—$R^7$; $C_1$–$C_6$-alkylene-$SO_3U$; $C_1$–$C_6$-alkylene-$PO_3U$; $C_1$–$C_6$-alkylene-$N(R^8)_3{}^+D^-$; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; a heteroaryl radical; V is a group —$CH_2$—$CH_2$—W—, —$CH_2CH_2CH_2W$—, —$CH(CH_3)$—$CH_2$—W—, —$CH_2$—$CH_2$—$CH_2$—$CH_2$—W— or —$CH_2$—$CH(CH_2CH_3)$—W—; D is Cl, Br, I or $SO_4R^9$; U is hydrogen, $Na^+$, $K^+$, $Mg^{2+}$, $Ca^{2+}$, $Li^+$, $Al^{3+}$ or —$N(R^8)_4{}^+$; W is O or NH; the radicals $R^7$ and $R^8$, which may be identical or different, are each hydrogen, a linear or branched $C_1$–$C_6$ alkyl radical; a linear or branched $C_2$–$C_6$ alkenyl radical; a linear or branched $C_1$–$C_6$ acyl radical; $R^9$ is hydrogen, a linear or branched $C_1$–$C_6$ alkyl radical; a $C_2$–$C_6$ alkenyl radical; n ranges from 1 to 3; and o ranges from 0 to 150.

15. The photostable cosmetic/dermatological composition as defined by claim 14, in which the compound of formula (VIII) has the formula (VIIIa) below:

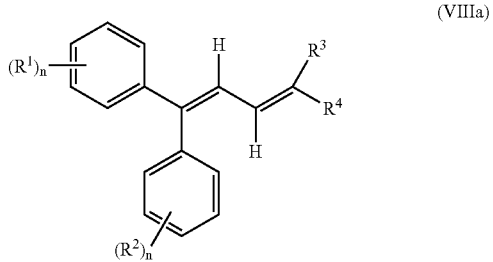

(VIIIa)

in which the diene system is of Z,Z; Z,E; E,Z or E,E configuration or mixtures of the said configurations, and in which the radicals $R^1$ and $R^2$, which may be identical or different, are each hydrogen, a $C_1$–$C_8$ alkyl radical; a $C_1$–$C_8$ alkoxy radical; a hydro-solubilizing substituent which comprises a carboxylate group, a sulfonate group or an ammonium residue; $R^3$ is a group $COOR^5$; $CONR^5R^6$; CN; $R^4$ is a group $COOR^6$; $CONR^5R^6$; $R^5$ is hydrogen; $[V]_o$—$R^7$; $C_1$–$C_6$-alkylene-$SO_3U$; $C_1$–$C_6$-alkylene-$N(R^8)_3{}^+D^-$; $R^6$ is $[V]_o$—$R^7$; $C_1$–$C_6$-alkylene-$SO_3U$; $C_1$–$C_6$-alkylene-$N(R^8)_3{}^+$ $D^-$; V is a —$CH_2$—$CH_2$—O—, —$CH_2CH_2CH_2O$—, —$CH(CH_3)$—$CH_2$—O— group; D is Cl, Br, I or $SO_4R^9$; U is hydrogen, $Na^+$, $K^+$, $Mg^{2+}$, $Ca^{2+}$, $Li^+$, $Al^{3+}$ or —$N(R^8)_4{}^+$ the radicals $R^7$, $R^8$ and $R^9$, which may be identical or different, are each hydrogen or a linear or branched $C_1$–$C_3$ alkyl radical; n ranges from 1 to 3; and o ranges from 0 to 50.

16. The photostable cosmetic/dermatological composition as defined by claim 14, in which the compound of formula (VIII) has the formula (VIIIb) below:

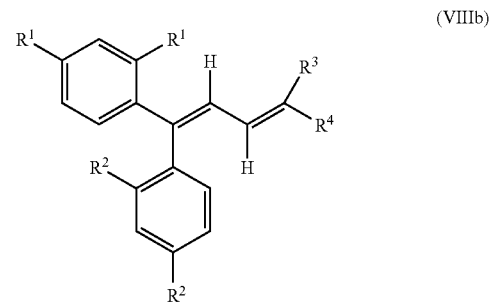

(VIIIb)

in which the diene system is of Z,Z; Z,E; E,Z or E,E configuration or mixtures of the said configurations, and in which the radicals $R^1$ and $R^2$, which may be identical or different, are each hydrogen, a $C_1$–$C_8$ alkyl radical; a $C_1$–$C_8$ alkoxy radical; $R^3$ is a group $COOR^5$; $CONR^5R^6$; CN; $R^4$ is a group $COOR^6$; $CONR^5R^6$; $R^5$ is hydrogen; $[V]_o$—$R^7$; $C_1$–$C_6$-alkylene-$SO_3U$; $C_1$–$C_6$-alkylene-$N(R^8)_3{}^+D^-$; $R^6$ is $[V]_o$—$R^7$; $C_1$–$C_6$-alkylene-$SO_3U$; $C_1$–$C_6$-alkylene-$N(R^8)_3{}^+$ $D^-$; V is a —$CH_2$—$CH_2$—O—, —$CH_2CH_2CH_2O$—, —$CH(CH_3)$—$CH_2$—O—group; D is Cl, Br, I or $SO_4R^9$; U is hydrogen, $Na^+$, $K^+$, $Mg^{2+}$, $Ca^{2+}$, $Li^+$, $Al^{3+}$ or —$N(R^8)_4{}^+$; the radicals $R^7$, $R^8$ and $R^9$, which may be identical or different, are each hydrogen or a linear or branched $C_1$–$C_3$ alkyl radical; and o ranges from 0 to 50.

17. The photostable cosmetic/dermatological composition as defined by claim 14, in which the compound of formula (VIII) has the formula (VIIIc) below:

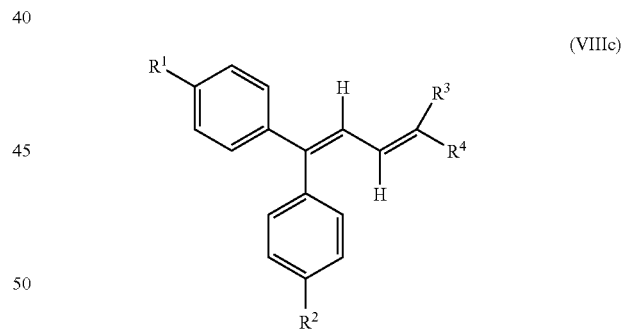

(VIIIc)

in which the diene system is of Z,Z; Z,E; E,Z or E,E configuration or mixtures of the said configurations, and in which the radicals $R^1$ and $R^2$, which may be identical or different, are each hydrogen, a $C_1$–$C_8$ alkyl radical; a $C_1$–$C_8$ alkoxy radical; $R^3$ is a group $COOR^5$; $CONR^5R^6$; CN; $R^4$ is a group $COOR^6$; $CONR^5R^6$; $R^5$ is hydrogen; $[X]_p$—$R^7$; $C_1$–$C_6$-alkylene-$SO_3Y$; $C_1$–$C_6$-alkylene-$N(R^8)_3{}^+D^-$; $R^6$ is $[V]_o$—$R^7$; $C_1$–$C_6$-alkylene-$SO_3U$; $C_1$–$C_6$-alkylene-$N(R^8)_3{}^+$ $D^-$; V is a —$CH_2$—$CH_2$—O—, —$CH_2CH_2CH_2O$—, —$CH(CH_3)$—$CH_2$—O— group; D is Cl, Br, I or $SO_4R^9$; U is hydrogen, $Na^+$, $K^+$, $Mg^{2+}$, $Ca^{2+}$, $Li^+$, $Al^{3+}$ or —$N(R^8)_4{}^+$; the radicals $R^7$, $R^8$ and $R^9$, which may be identical or different, are each hydrogen or a linear or branched $C_1$–$C_3$ alkyl radical; and ranges from 0 to 50.

18. The photostable cosmetic/dermatological composition as defined by claim 14, in which the compound of formula (VIII) is selected from among the following compounds:

(6)
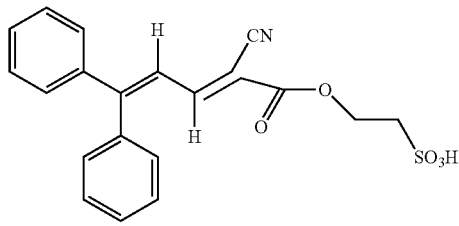

(7)
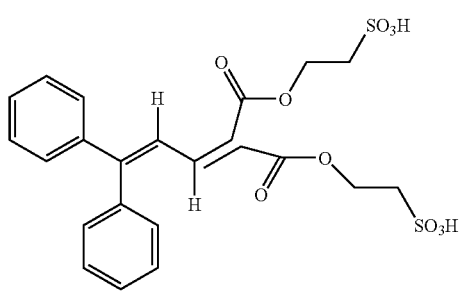

(8)
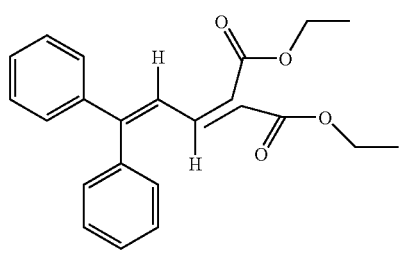

(9)
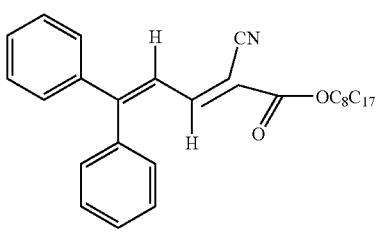

(10)
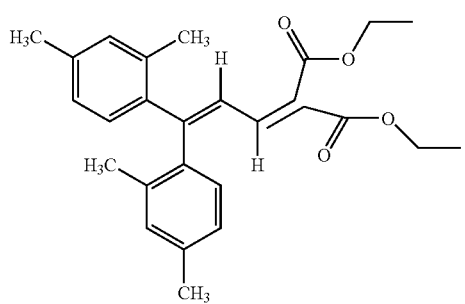

19. The photostable cosmetic/dermatological composition as defined by claim 1, said at least one 4,4-diarylbutadiene compound comprising an oligomer having the formula (IX) below:

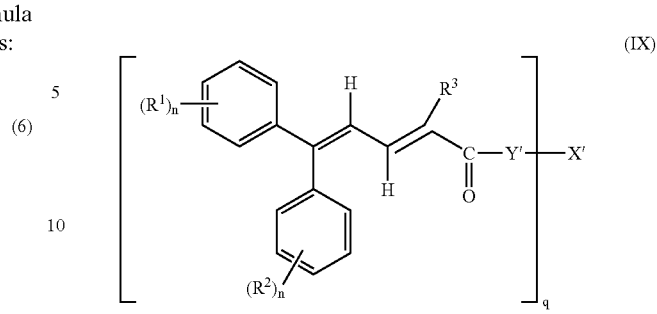
(IX)

in which the diene system is of Z,Z; Z,E; E,Z or E,E configuration or mixtures of the said configurations, and in which the radicals $R^1$, $R^2$, $R^3$ and n have the same definitions as in formula (VIII); Y' is a group —O— or —$NR^{10}$—; $R^{10}$ is hydrogen; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; a heteroaryl radical; X' is an aliphatic or cycloaliphatic linear or branched polyol residue comprising from 2 to 10 hydroxyl groups and of valency q; the carbon-based chain of the said residue optionally being interrupted with one or more sulfur or oxygen atoms; one or more imine groups; one or more $C_1$–$C_4$ alkylimino groups; and q ranges from 2 to 10.

20. The photostable cosmetic/dermatological composition as defined by claim 19, wherein the oligomer of formula (IX), the radicals $R^1$ and $R^2$, which may be identical or different, are each hydrogen, a $C_1$–$C_{12}$ alkyl radical; a $C_1$–$C_8$ alkoxy radical; a hydro-solubilizing substituent which comprises a carboxylate group, a sulfonate group or an ammonium residue; $R^3$ is a group $COOR^5$; $CONR^5R^6$; CN; a $C_3$–$C_{10}$ cycloalkyl radical; a $C_7$–$C_{10}$ bicycloalkyl radical; the radicals $R^5$ and $R^6$, which may be identical or different, are each a linear or branched $C_1$–$C_{20}$ alkyl radical; a $C_3$–$C_{10}$ cycloalkyl radical; a $C_7$–$C_{10}$ bicycloalkyl radical; optionally substituted naphthyl or phenyl; and X' is a polyol residue comprising from 2 to 6 hydroxyl groups.

21. The photostable cosmetic/dermatological composition as defined by claim 20, wherein said oligomer of formula (IX), X' is an ethanol or pentaerythrol residue.

22. The photostable cosmetic/dermatological composition as defined by claim 19, said at least one oligomer of formula (IX) comprising at least one of the following compounds:

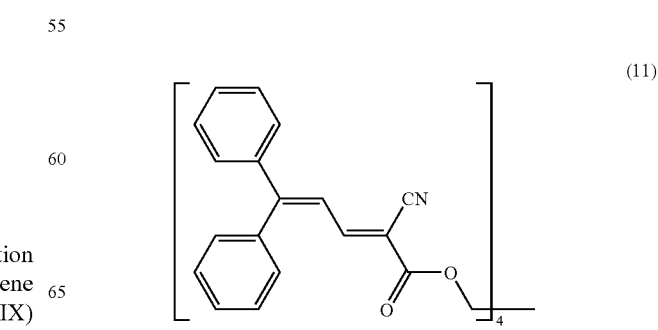
(11)

-continued (12)

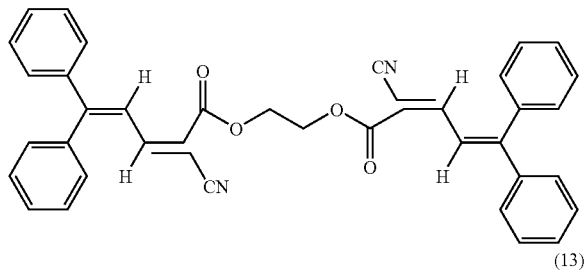

(13)

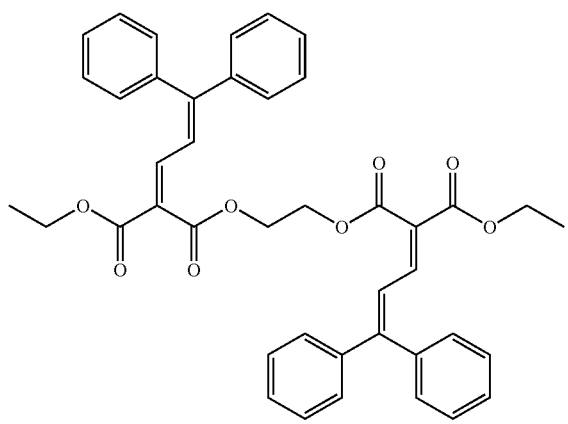

23. The photostable cosmetic/dermatological composition as defined by claim 1, further comprising at least one other UV-A-active and/or UV-B-active organic screening agent.

24. The photostable cosmetic/dermatological composition as defined by claim 23, said at least one organic UV-screening agent being selected from the group consisting of anthranilates; salicylic derivatives; camphor derivatives; benzophenone derivatives; β,β'-diphenylacrylate derivatives; benzotriazole derivatives; non-photosensitive triazine derivatives; benzimidazole derivatives; benzalmalonate derivatives; imidazolines; bis-benzazolyl derivatives; p-aminobenzoic acid (PABA) derivatives; methylenebis(hydroxyphenyl)benzotriazole derivatives; screening polymers and screening silicones; dimers derived from α-alkylstyrene, and mixtures thereof.

25. The photostable cosmetic/dermatological composition as defined by claim 24, said at least one other organic UV-screening agent being selected from the group consisting of:
Ethylhexyl salicylate,
Octocrylene,
Phenylbenzimidazolesulfonic acid,
Terephthalylidenedicamphorsulfonic acid,
Benzophenone-3,
Benzophenone-4,
Benzophenone-5,
4-Methylbenzylidenecamphor,
Disodium phenyl dibenzimidazole tetrasulfonate,
Anisotriazine,
2,4,6-tris(Diisobutyl 4'-aminobenzalmalonate)-s-triazine,
Methylenebis(benzotriazolyl)tetramethylbutyl-phenol,
Drometrizole trisiloxane, and mixtures thereof.

26. The photostable cosmetic/dermatological composition as defined by claim 1, further comprising at least one coated or uncoated metal oxide pigment or nanopigment.

27. The photostable cosmetic/dermatological composition as defined by claim 26, said at least one UV-screening pigment or nanopigment comprising titanium oxide, zinc oxide, iron oxide, zirconium oxide, cerium oxide, and mixtures thereof.

28. The photostable cosmetic/dermatological composition as defined by claim 1, further comprising at least one agent for artificially tanning and/or browning the skin.

29. The photostable cosmetic/dermatological composition as defined by claim 1, further comprising at least one adjuvant or additive selected from the group consisting of fatty substances, organic solvents, ionic or nonionic thickeners, softeners, antioxidants, free-radical scavengers, opacifiers, stabilizers, emollients, silicones, α-hydroxy acids, antifoams, moisturizers, vitamins, insect repellants, fragrances, preservatives, surfactants, anti-inflammatories, substance P antagonists, fillers, polymers, propellants, acidifying or basifying agents, colorants, and mixtures thereof.

30. The photostable cosmetic/dermatological composition as defined by claim 1, formulated for photoprotecting the human epidermis and comprising a nonionic vesicular dispersion, an emulsion, a cream, a milk, a gel, a cream-gel, a suspension, a dispersion, a powder, a solid, a mousse or a spray.

31. The photostable cosmetic/dermatological composition as defined by claim 1, formulated as a makeup for the eyelashes, the eyebrows or the skin and formulated as solid or pasty, anhydrous or aqueous formulation, or an emulsion, a suspension or a dispersion.

32. The photostable cosmetic/dermatological composition as defined by claim 1, formulated for photoprotecting the hair against ultraviolet rays and comprising a shampoo, a lotion, a gel, an emulsion or a nonionic vesicular dispersion.

33. A regime or regimen for photoprotecting the skin and/or hair against the damaging effects of UV radiation, comprising topically applying thereon an effective amount of the photostable cosmetic/dermatological composition as defined by claim 1.

34. A method for enhancing the UV photostability of a 1,3,5-triazine compound that is photosensitive in the presence of a dibenzoylmethane sunscreen, comprising formulating therewith an effective amount of at least one 4,4-diarylbutadiene compound.

* * * * *